United States Patent [19]
Greenberg et al.

[11] Patent Number: 5,944,747
[45] Date of Patent: Aug. 31, 1999

[54] METHOD FOR PREFERENTIAL OUTER RETINAL STIMULATION

[75] Inventors: Robert J. Greenberg, Los Angeles, Calif.; Mark S. Humayun, Baltimore; Eugene de Juan, Jr., Phoenix, both of Md.

[73] Assignee: Johns Hopkins University, Baltimore, Md.

[21] Appl. No.: 09/041,932

[22] Filed: Mar. 13, 1998

[51] Int. Cl.$^6$ .................................................. A61N 1/32
[52] U.S. Cl. .................................................. 607/54
[58] Field of Search ......................................... 607/53, 54

[56] References Cited

U.S. PATENT DOCUMENTS

| | | | |
|---|---|---|---|
| 4,628,933 | 12/1986 | Michelson | 128/419 |
| 4,664,117 | 5/1987 | Beck | 128/420 |
| 4,918,745 | 4/1990 | Hutchinson | 455/41 |
| 4,979,508 | 12/1990 | Beck | 128/419 |
| 5,016,633 | 5/1991 | Chow | 128/419 |
| 5,024,223 | 6/1991 | Chow | 128/419 |
| 5,109,844 | 5/1992 | de Juan, Jr. et al. | 128/419 |
| 5,147,284 | 9/1992 | Fedorov et al. | 600/9 |
| 5,159,927 | 11/1992 | Schmid | 128/419 |
| 5,397,350 | 3/1995 | Chow et al. | 623/4 |
| 5,411,540 | 5/1995 | Edell et al. | 607/53 |
| 5,476,494 | 12/1995 | Edell et al. | 607/116 |
| 5,522,864 | 6/1996 | Wallace et al. | 607/53 |
| 5,554,187 | 9/1996 | Rizzo, III | 623/6 |
| 5,556,423 | 9/1996 | Chow et al. | 607/54 |
| 5,575,813 | 11/1996 | Edell et al. | 607/116 |
| 5,597,381 | 1/1997 | Rizzo, III | 623/4 |
| 5,674,263 | 10/1997 | Yamamoto et al. | 607/54 |

FOREIGN PATENT DOCUMENTS

| | | | |
|---|---|---|---|
| PCT/US96/08734 | 12/1996 | WIPO | A61N 1/05 |
| PCT/US96/13277 | 2/1997 | WIPO | A61F 2/16 |

OTHER PUBLICATIONS

Investigative Opthalmology & Visual Science pamphlet, Mar. 15, 1997, vol.38, No. 4.

Clinical Sciences Magazine, Jan. 1996 issue, vol. 114, pp. 40–46, entitled Visual Perception Elicited by Electrical Stimulation of Retina in Blind Humans.

Publications entitled "Selective electrical stimulation of retinal neurons by varying stimulus pulse duration", dated Jul. 28, 1997.

Publication entitled "A Computational Model of Electrical Stimulation of the Retinal Ganglion Cell", dated Jun. 11, 1996.

Publication entitled "Dual Unit Visual Intraocular Prosthesis" for IEEE/EMBS, 19$^{th}$ International Conference, Oct. 30–Nov. 2, 1997, pp. 2303–2306.

Publication entitled "Electrode geometry design for a retinal prosthesis".

Primary Examiner—Scott M. Getzow
Attorney, Agent, or Firm—Leydig, Voit & Mayer, Ltd.

[57] ABSTRACT

A method of focused phosphene generation through deeper intermediate retinal cellular electrical stimulation to the exclusion of direct ganglion cellular electrical stimulation comprises the steps of: a) positioning a stimulating electrode in the vicinity of retinal tissue; and b) applying a long duration stimulation signal to the electrode such that deeper intermediate retinal cells are preferentially stimulated over the retinal ganglion cells and proximal overlying surface axons. The long duration stimulation signal is preferably a biphasic signal having a negative and a positive phase pulse which is applied in cathodic fashion. To preferentially stimulate the deeper intermediate retinal elements the duration of the long duration stimulation signal is greater than 0.5 millisecond per phase pulse, and preferably equal to or longer than 2 millisecond per phase pulse. The biphasic signal is preferably adjusted to simulate a monophasic signal by adjusting the magnitude of the negative pulse in relation to positive pulse, and by adjusting the duration of the positive pulse in relation to the negative pulse to maintain approximately net zero charge introduction. Preferably, the ratio of the negative pulse to the positive pulse is approximately 10:1 or greater.

20 Claims, 6 Drawing Sheets

METHOD FOR PREFERENTIAL OUTER RETINAL STIMULATION

TECHNICAL FIELD OF THE INVENTION

This invention relates to outer retinal stimulation to produce phosphenes, and more particularly to a method of electrical stimulation of selected retinal cells to the exclusion of other retinal cells to produce phosphenes.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concepts of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, the phosphenes which were perceived were unfocused and could not approach actual vision restoration or simulation because of the gross, unfocused stimulation of the patient's eye or the optical nerve.

As intraocular surgical techniques advanced, it became possible to apply a more focused stimulation on small groups of, and even on individual, retinal cells to generate focused phosphenes. This focused phosphene generation opens the possibility of true simulated vision generation by an implanted prosthesis within the eye itself. This has sparked renewed interest in developing methods and apparatuses to aid the visually impaired. Specifically, great effort has been expended in the area of focused stimulation of retinal elements proximal to degenerated photoreceptors which occur in certain forms of retinal blindness and which affect millions of people worldwide. However, while the surgical techniques had advanced to the point of allowing access to the retina, and while the structure and function of the retinal cells was understood, a complete understanding of the individual processes and mechanisms of simulated vision through retinal cellular stimulation was not completely understood in these early days.

What was known about the structure of the retina is that the retinal basement membrane 10 (see FIG. 1) is at the surface of the retina, above the axons 11 which emanate from the retinal ganglion cells 12. These axons 11 which emanate from the retinal ganglion cells eventually come together and form the optic nerve (not shown) which projects to the brain. Beneath the retinal ganglion cells 12 are nerve cells involved in intermediate signal processing, such as amacrine cells 13, bipolar cells 14, interplexiform cells 15, and horizontal cells 16. At the back or outer layer of the retina are the photoreceptor cells 17. In degenerative diseases of the retina, such as retinitis pigmentosa, the photoreceptor cells 17 degrade, but the other nerve cells remain viable.

Pioneering work by de Juan, Jr. et al. embodied in U.S. Pat. No. 5,109,844 for RETINAL MICROSTIMULATION which issued May 5, 1992, provided the teaching for a method for stimulating the still viable retinal cells as well as for an apparatus for practicing this method, said teachings and disclosure being hereby incorporated by reference. As taught by de Juan, Jr. et al. '884, a focused stimulation of the retinal ganglion cells 12 could produce focused phosphenes which, if stimulated by an array apparatus, could simulate vision. De Juan, Jr. et al. '844 also teaches that the stimulation current capable of penetrating the retina to an excitation depth of approximately 30 micrometers is sufficient to depolarize the ganglion cells and evoke an action potential therefrom, the patient's perception of which is a focused phosphene. While de Juan, Jr. et al. '844 does not dwell on the stimulation waveform, this patent does teach that the waveform should preferably have an amplitude of not greater than about 0.3 to 3 milliampere and be biphasic having pulse duration of about 0.1 to about 2 milliseconds per phase, with a frequency of about 50 to 100 hertz.

Since the axons from the ganglion cells traverse the surface of the retina on their way to form the optic nerve as discussed briefly above, it is recognized that to produce a focused phosphene, inadvertent stimulation of axons from distant ganglion cells which lie adjacent the target ganglion cells must be avoided. An inadvertent stimulation of adjacent axons from distant ganglion cells results in the perception of a wedge of light as opposed to a focused point of light and makes clear simulated vision through a retinal prosthesis difficult to obtain.

One method of focused retinal cell stimulation which attempts to avoid the problem of inadvertent adjacent axon stimulation is described in Edell et al., U.S. Pat. No. 5,411,540, issued May 2, 1995, for a METHOD AND APPARATUS FOR PREFERENTIAL NEURON STIMULATION. Edell et al. '540 describes the use of anodic (positive) stimulation to preferentially stimulate retinal ganglia somas while simultaneously avoiding unwanted stimulation of nearby unrelated axons to produce a focused phosphene. This reference describes that this positive pulse scheme requires a waveform pulse of duration between about 1 microsecond and about 500 microsecond having an amplitude of between about 1 microampere and about 500 microampere at a frequency of up to 1 kHz. Edell et al. '540 also teaches that the particular geometry of the electrode has a direct impact on the effectiveness of its method of stimulation of the ganglia soma and on the inadvertent and undesired stimulation of unrelated superficial axons from distant retinal ganglia soma. Edell et al. '540, therefore, requires specific geometry electrodes to perform the focused stimulation. However, the added complexity resulting from the criticality of placement and specific geometry of the electrodes, as well as the potential cellular effects of anodic (positive) stimulation and likely inadvertent stimulation of unrelated axons anyway, make this approach less desirable.

BRIEF SUMMARY OF THE INVENTION

It is an object of the instant invention to overcome at least some of the aforementioned and other known problems existing in the art. More particularly, it is an object of the instant invention to provide a new and improved method of producing focused phosphenes. Additionally, it is an object of the instant invention to provide a method of producing focused phosphenes which avoids the problems of inadvertent stimulation of proximal surface axons from distant ganglia soma.

In view of these objects, it is a feature of the instant invention to provide a method of producing focused phosphenes which do not directly stimulate surface ganglia soma or proximal axon in the region of stimulation. More particularly, it is a feature of the instant invention to provide a method of generating focused phosphenes by stimulating retinal elements below the ganglion cells and their surface axons. Further, it is a feature of the instant invention to provide a method of producing focused phosphenes by stimulating intermediate retinal cells such as bipolar cells.

It is therefore an aspect of the invention to provide a method of producing a focused phosphene by stimulating intermediate level retinal cells by varying the pulse duration of the stimulation signal. More particularly, it is an aspect of the instant invention to increase the duration of the stimulation signal pulse width to selectively directly stimulate only the deeper intermediate retinal cells. Further, it is an aspect of the instant invention to stimulate these deeper intermediate retinal cells by utilizing a vitreous-cathodic stimulation. Additionally, it is an aspect of the instant invention to utilize biphasic pulses. Furthermore, it is an aspect of the instant invention to make these biphasic pulses simulate cathodic monophasic pulses by using unequal amplitude phases. It is a further aspect of the instant invention to utilize an equal total charge in each phase to avoid damage to the underlying neural tissue from electrochemical effects.

In a preferred embodiment of the instant invention, a method of focused phosphene generation through deeper intermediate retinal cellular electrical stimulation to the exclusion of direct ganglion cellular electrical stimulation is provided which comprises the steps of: a) positioning a stimulating electrode in the vicinity of retinal tissue; and b) applying a long duration stimulation signal to the electrode such that deeper intermediate retinal cells are preferentially stimulated over the retinal ganglion cells and proximal overlying surface axons. The long duration stimulation signal is preferably a biphasic signal having a negative and a positive phase pulse which is applied in cathodic fashion. To preferentially stimulate the deeper intermediate retinal elements, the duration of the long duration stimulation signal is greater than about 0.5 millisecond per phase pulse, and preferably equal to or longer than about 2 millisecond per phase pulse. In a highly preferred embodiment of the instant invention, the biphasic signal is adjusted to simulate a monophasic signal by adjusting the magnitude of the negative pulse in relation to positive pulse, and by adjusting the duration of the positive pulse in relation to the negative pulse to maintain approximately net zero charge introduction. Preferably, the ratio of the negative pulse magnitude to the positive pulse magnitude is approximately 10:1 or greater.

In an alternate embodiment of the instant invention, a method of producing focused phosphenes is presented which comprises the steps of: 1) positioning a stimulating electrode in proximity to retinal tissue; 2) generating a biphasic stimulation signal having a negative and a positive pulse and including an intra-pulse delay therebetween, each of the pulses having a duration equal to or greater than about 2 milliseconds and a magnitude, the biphasic stimulation signal having a relationship between the magnitude and the duration of the negative and the positive pulses such that the total charge supplied is approximately zero; and 3) applying the biphasic stimulation signal to the electrode in a cathodic fashion.

These and other aims, objectives, and advantages of the invention will become more apparent from the following detailed description while taken into conjunction with the accompanying drawings.

Figure 1:
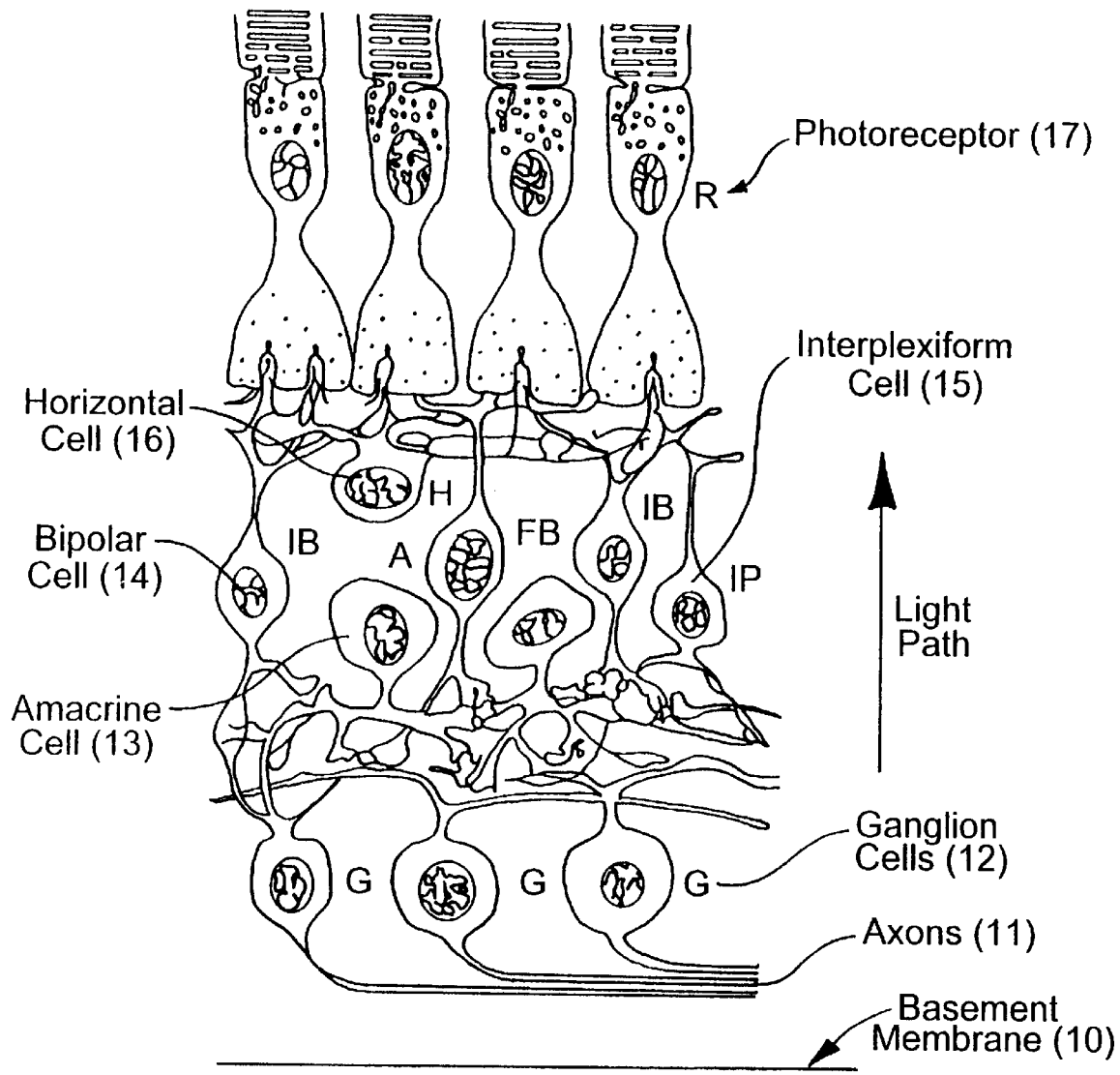
FIG. 1 is a side sectional illustration of the retina in substantially anatomically correct form with the natural path of light in the retina indicated by the arrow.

While the invention is susceptible of various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions, methods, and equivalents falling within the spirit and scope of the invention as defined by the appended claims.

DETAILED DESCRIPTION OF THE PREFERRED EMBODIMENT

To fully appreciate the instant invention, it is instructive to return to the simplified cross-sectional view of the retina illustrated in FIG. 1. In vertebrate animals, including humans, retinal ganglion cells 12 (RGCs) lie close to the surface of the retina facing the vitreous cavity and send mostly unmyelinated axons 11 in a more superficial layer toward the optic disc (not shown). As the human RGC axons exit the eye, they become myelinated and form the optic nerve. The cell bodies (somas) of these ganglion cells 12 are mapped over the surface of the retina in a manner which approximates the projection of the visual world onto the surface of the retina. However, at any particular location on the surface of the retina, axons 11 from distant sites overlie the individual ganglion cell bodies.

Figure 2:
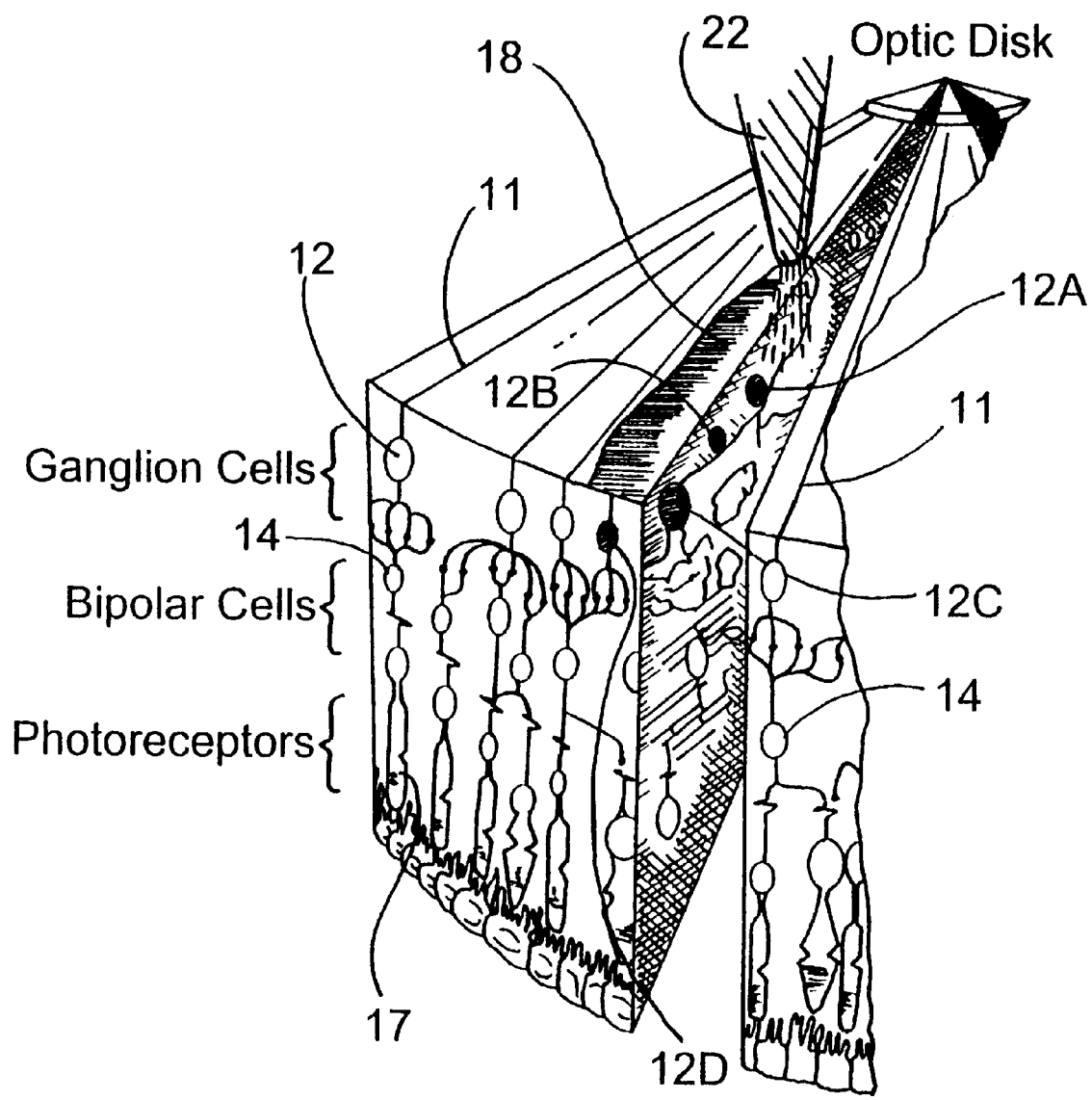
FIG. 2 is a simplified schematic representation of a region of neural retinal tissue being stimulated by an electrode placed on the vitreous surface of the retina and which is stimulating the ganglion cell axon, the stimulated portion being illustrated as a shaded area.

If these superficial passing fibers 11 were inadvertently stimulated by a surface electrode 22 while attempting to stimulate only proximal retinal ganglia soma, entire groups of ganglion cells 12a–d from a large area of the retina would be excited, illustrated in FIG. 2 as the shaded area labeled 18. The visual perception of such a resultant distributed stimulation would be in the form of a wedge of light, and not of a focused spot of light. On the other hand, if only the ganglion cell 12 near the cell bodies could be preferentially stimulated, illustrated in FIG. 3 as the shaded area labeled 20, the visual perception of a focal spot (focused phosphene) would be expected. However, such selected stimulation of only the ganglion cell without also inadvertently stimulating the proximal overlying surface axons 11 is difficult as discussed above.

Figure 3:
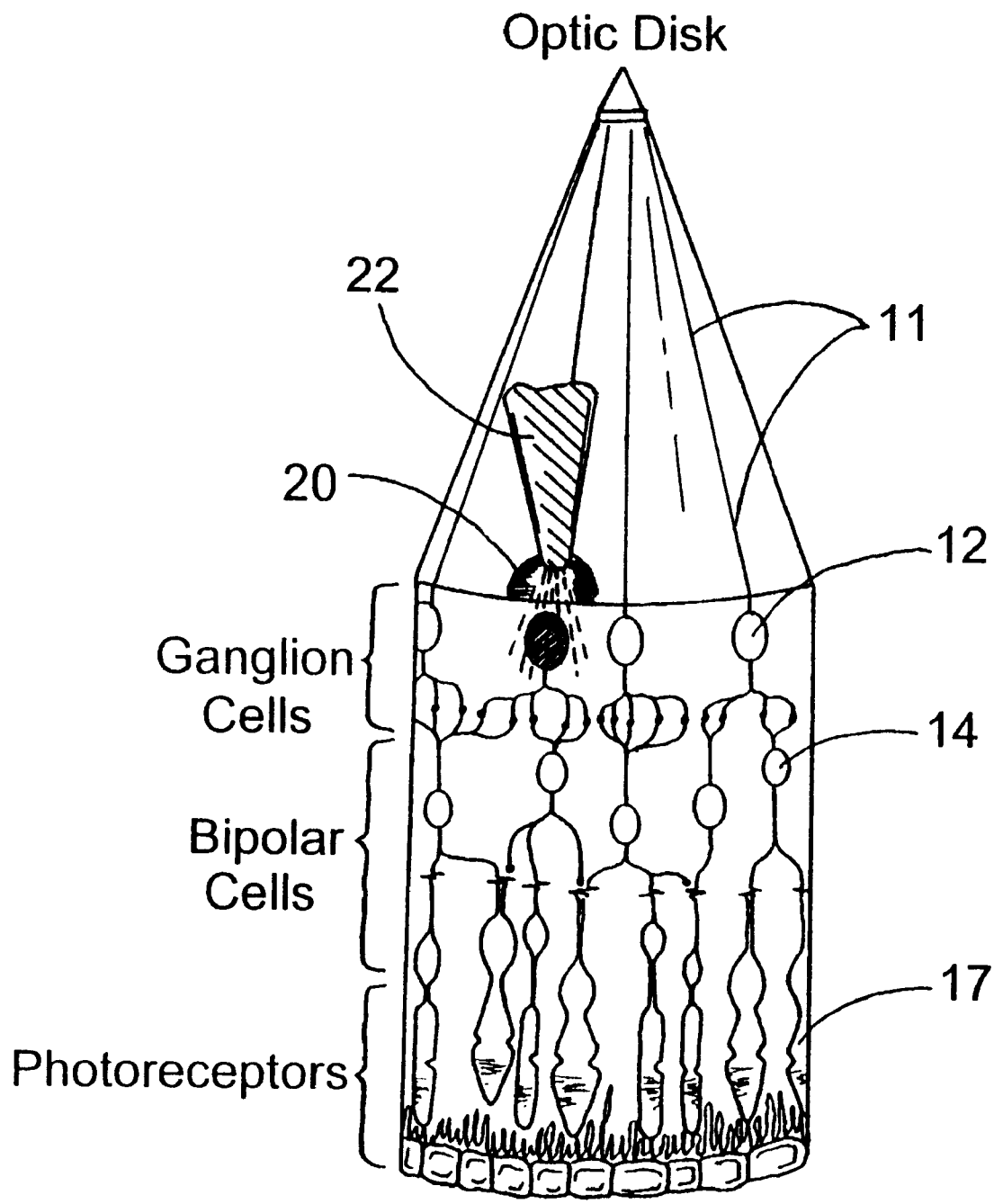
FIG. 3 is a simplified schematic representation of a region of neural retinal tissue being stimulated by an electrode placed on the vitreous surface of the retina and which is stimulating the ganglion cell soma, the stimulated portion being illustrated as a shaded area.
Figure 4:
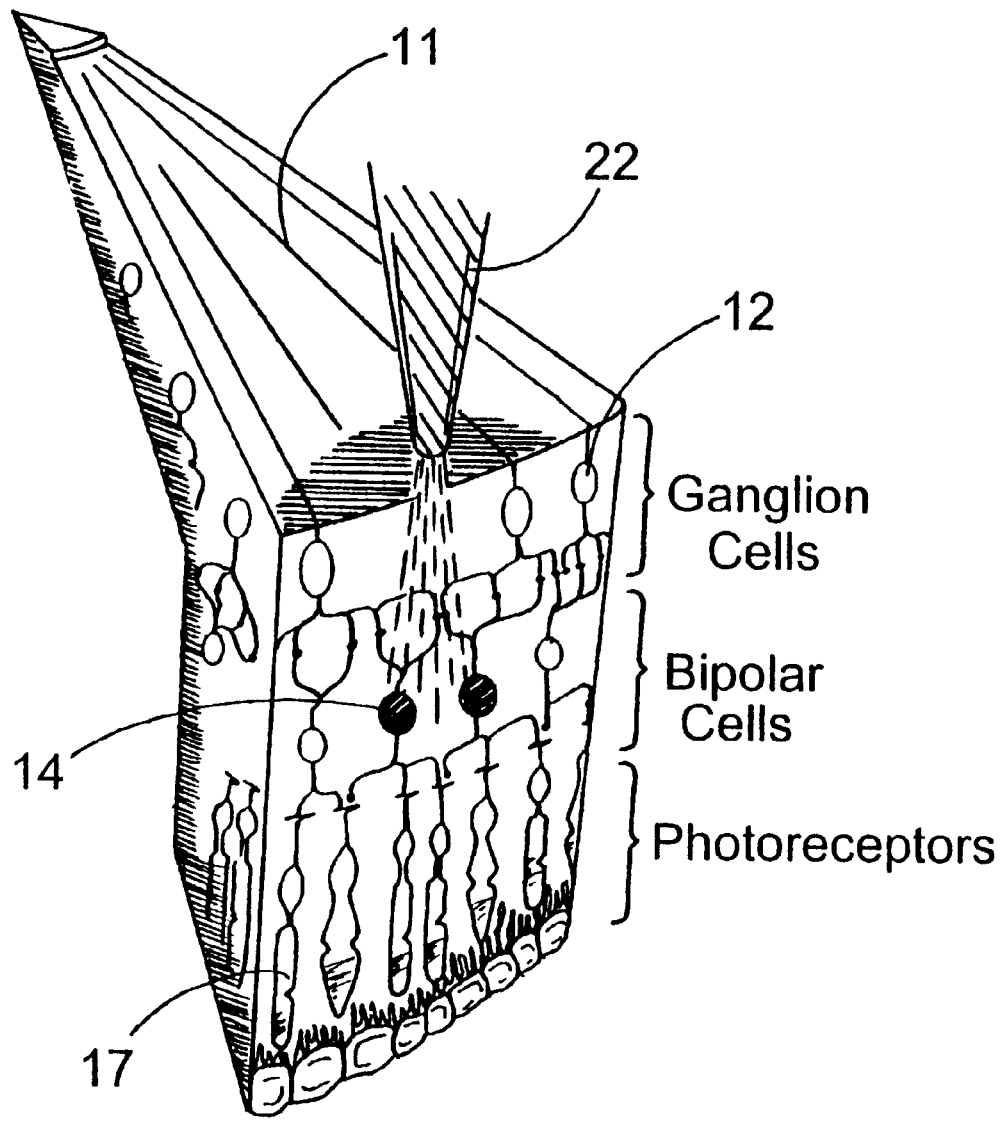
FIG. 4 is a simplified schematic representation of a region of neural retinal tissue being stimulated in accordance with the method of the instant invention by an electrode placed on the vitreous surface of the retina and which is stimulating the deeper intermediate retinal cells such as the bipolar cells, the stimulated portion being illustrated as a shaded area.

In accordance with a preferred method of the instant invention, however, direct stimulation of the ganglion cells and the problem of inadvertent stimulation of the overlying surface axons is avoided by electrical stimulation of deeper retinal cells, such as the bipolar cells 14 or other deeper retinal cells illustrated in FIG. 4. The visual perception of this type of retinal stimulation is also a focal spot, although slightly larger than that which might be produced by stimulation of only a single ganglion cell. However, the focal spot diameter is sufficiently small to allow use in a retinal prosthesis, while avoiding all of the problems associated with surface ganglion stimulation and inadvertent proximal axon stimulation. It should be noted that the stimulating electrode 22 in each of FIGS. 2, 3, and 4 is illustrated schematically only as its particular configuration forms no part of this invention.

In developing such a deep retinal cellular stimulation method of the instant invention, it was discovered that, unlike other neural systems of the body, the time constants of retinal cells are significantly different from one another, which has a profound effect on the electrically elicited retinal responses. Where cells with different time-constants are in close physical proximity, for example, nerve vs. muscle, it has been observed that long time-constant cells are stimulated preferentially with long pulses whereas cells with short time-constants are stimulated preferentially with short pulses.

Through experimentation the inventors have determined that, in the retina, short stimulus durations directly stimulate retinal ganglion cells (RGCs) while longer stimulus pulses target deeper cell to the exclusion of the surface RGCs and the proximal axons. With such a recognition, a method in accordance with the instant invention may be utilized to produce focused phosphenes by deep retinal cell stimulation while totally avoiding the problem of inadvertent overlying proximal axon stimulation. This deep retinal cell stimulation also reveals advantages when the post-mortem histology of the entire retina in patients with retinitis pigmentosa (RP) is considered. This histology indicates a significant preservation of deeper (inner nuclear layer) retinal cells. In the most severe cases of RP in patients with no light perception at all, the outer nuclear layer (photoreceptors) retained only about 5% of cells, the inner nuclear layer (bipolar cells and others) retained about 78% of cells, and the RGC layer retained only about 30% of cells. Thus the stimulation of this vastly more populated region containing many more active cells significantly improves the ability of a retinal prosthesis to enhance or produce simulated vision in patients suffering from RP or other visual degenerative conditions.

To isolate the stimulation parameters to allow preferential stimulation of these deeper retinal cells, the latency from stimulation was measured under varying stimulation conditions. This was done because a neuronal impulse initiated at the level of deeper retinal cells has to traverse at least one synapse before initiating a RGC action potential, resulting in longer RGC latencies than direct stimulation of the RGC. However, since the latencies in patients with RP cannot be measured when these patients are awake with normal eye movements, another measure for the target cell is needed. By measuring the response threshold for various stimulus durations, a strength-duration curve (S-D curve) can be constructed.

Figure 5:
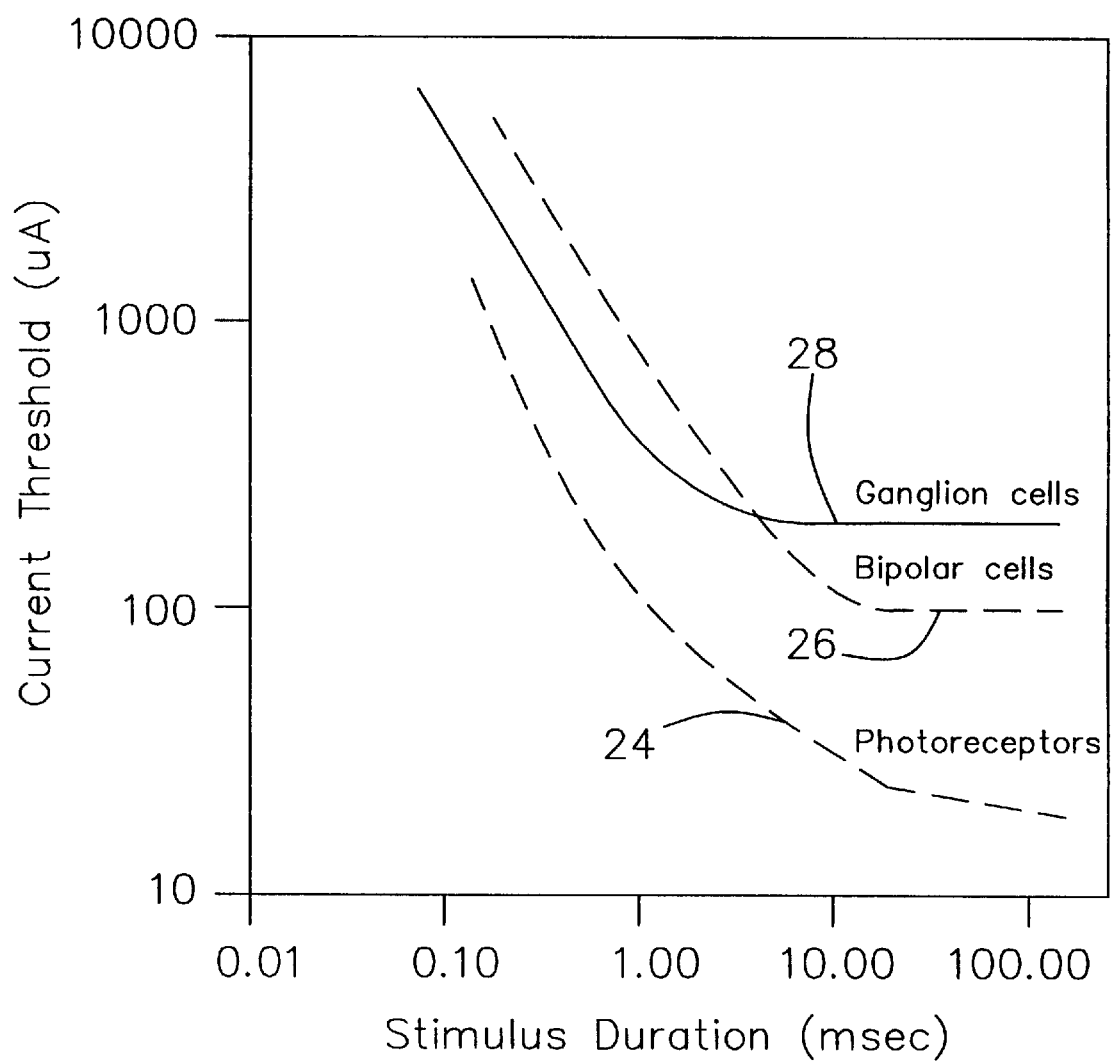
FIG. 5 is a graphical illustration of an average of experimental data recorded in frog retinas of the stimulation strength versus stimulation pulse duration required to generate a biologic response for stimulation of different layers of the retina.

One such curve is illustrated as FIG. 5 and was generated using frog retina to establish the characteristics of the stimulation of each type of cell, the photoreceptors (trace 24), the bipolar cells (trace 26), and the ganglion cells (trace 28). As may be seen, the photoreceptors are by far the easiest retinal elements to stimulate, i.e., they have the lowest stimulation current thresholds. In certain diseases called outer retinal degenerations, however, the photoreceptors are damaged, leaving only ganglion cells, bipolar cells, and other deeper intermediate retinal cells. In cases of outer retinal degeneration, it is possible to select ganglion cells by using short duration pulses. In accordance with a method of the instant invention, it is also possible to stimulate deeper retinal cells by using longer duration stimuli. As the relationship depicted in FIG. 5 illustrates, this longer stimuli can be accomplished at reduced current threshold levels as well, which may seem counterintuitive due to the increased distance from the source of stimulation to the deeper retinal cells.

For neurons, these strength-duration curves have a hyperbolic shape and can be characterized by a time-constant and asymptote. Two terms often used to refer to these parameters are the chronaxie and rheobase. The chronaxie is uniquely determined by the element stimulated, and varies only slightly with the stimulus parameters and electrode geometry. To determine the time-constant and rheobase from actual data, the strength-duration curve is fit using a weighted Marquardt-Levenberg algorithm to the following equation:

$$I_{threshold} = \frac{I_{rheobase}}{(1 - e^{t/\tau})}$$

where $\tau T$ is the time-constant. The chronaxie is the pulse duration when the threshold stimulus is twice the rheobase and is actually $\ln(2) \times \tau$. In human patients suffering from RP, experimentation revealed a chronaxie of 6.1±2.8 millisecond. These long chronaxies found in RP patients seem to rule out the possibility of RGC stimulation with long pulses, and evidence that deeper cells, such as bipolar cells, are the target of longer duration stimulation pulses. Ganglion cells would be expected to have a chronaxie of less than 1 millisecond like other central nervous system neurons, whereas non-spiking deeper cells have longer chronaxies. By stimulating these more distal retinal elements, long cathodic pulses offer the advantage to a retinal prosthesis of incorporating more of the natural retinal processing of the visual signal through the various retinal cells, while simultaneously avoiding inadvertent superficial axonal stimulation.

Figure 6:
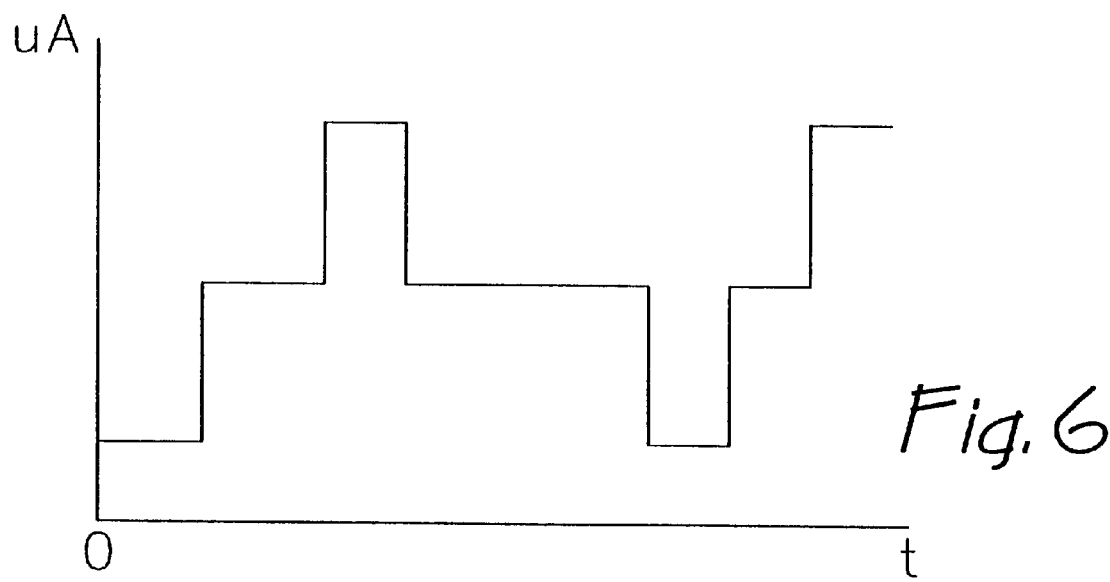
FIG. 6 is a graphical signal chart illustrating an embodiment of the stimulation signal used to generate focused phosphenes by electrical stimulation of deeper intermediate retinal cells to the exclusion of the direct stimulation of the surface ganglion cells in accordance with the instant invention.

With regard to the stimulation pulses, it is important to deliver balanced biphasic current pulses to patients to reduce the biologically harmful product of electrochemical reactions. Practicing a preferred method of the instant invention, the pulses are delivered with the cathodic pulse first as illustrated in FIG. 6. The delay between the two phases of current (intra-pulse) may be in relation to the pulse durations themselves, or may preferably be in the range of about 1 to 4 millisecond. The delay may also be timed to allow time for the stimulated deeper intermediate retinal cells to respond to the stimulation before equalizing the cellular charge by the introduction of the positive pulse. It should be noted, however, that while a preferred embodiment can utilize a biphasic pulse with an intra-pulse delay as just described, a biphasic pulse with no intra-pulse delay can also be utilized in practicing the instant invention.

Figure 7:
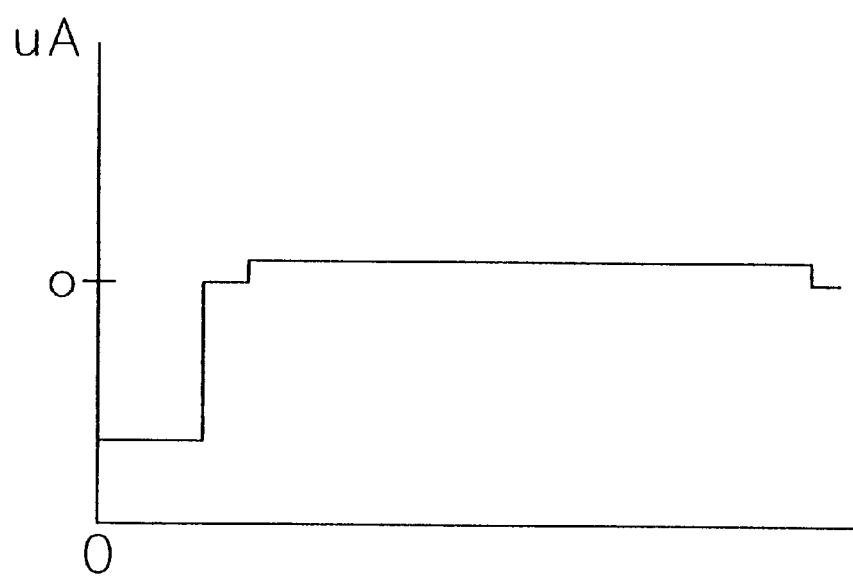
FIG. 7 is a graphical signal chart illustrating an alternate embodiment of the stimulation signal simulating a monophasic signal and used to generate focused phosphenes by electrical stimulation of deeper intermediate retinal cells to the exclusion of the direct stimulation of the surface ganglion cells in accordance with the instant invention.

Additionally, to effect monophasic stimulation (simulated monophasic stimulation), the relative height of the two pulses may be varied relative to one another. The larger the relative difference in magnitude, the more closely monophasic type stimulation is simulated. Preferably, the amplitudes are adjusted so that one pulse is about 10 times the amplitude of the other as illustrated in FIG. 7, although one skilled in the art will recognize that other ratios can be utilized. When this type of simulated monophasic stimulation is utilized, the pulse durations are adjusted so that the injected charge is still balanced, that is to say, no net charge is injected.

Specifically, a preferred method of focused phosphene generation through deeper intermediate retinal cellular electrical stimulation to the exclusion of direct ganglion cellular electrical stimulation comprises the steps of: a) positioning a stimulating electrode in the vicinity of the retinal tissue; and b) applying a long duration stimulation signal to the electrode such that deeper intermediate retinal cells are preferentially stimulated over the retinal ganglion cells and proximal overlying surface axons. The magnitude and duration of the stimulation signal may be selected to preclude inadvertent stimulation of retinal ganglion cells by selecting a sufficiently long duration signal at a low current threshold below which the ganglion cells require for that duration signal (see FIG. 5). Preferably, the stimulation signal is a biphasic signal as discussed above, applied in a cathodic fashion (negative pulse first).

The duration of the biphasic pulses of the long duration stimulation signal is preferably greater than 0.5 millisecond per phase pulse. In a preferred embodiment of the instant invention, the duration is equal to or greater than about 2 millisecond per phase pulse. In a further embodiment, the duration is greater than about 4 millisecond per phase pulse, and preferably greater than about 8 millisecond per phase pulse. The long duration stimulation signal can be composed of a train of these pulses. Additionally, the stimulation signal can be a low frequency signal having a frequency less than about 2 kilohertz. Preferably, the low frequency signal has a frequency of less than or equal to about 500 hertz, and preferably less than about 125 hertz. Furthermore, the stimulation signal can have a frequency of about 50 hertz or less.

Additionally, a preferred method includes an intra-pulse delay. The duration of this intra-pulse delay may be in relation to the pulse duration or may be fixed. Preferably, the intra-pulse delay ranges between about 1 to 4 millisecond. In a further embodiment of a preferred method of the instant invention, the stimulation signal is generated to simulate a cathodic monophasic stimulation pulse. In so doing, the relative magnitude of the stimulation pulses are adjusted in relation to one another. Preferably, the relative magnitude is on the order of 10:1. To maintain a net zero charge injection, the duration of the unequal magnitude pulses are varied accordingly.

Numerous modifications and alternative embodiments of the invention will be apparent to those skilled in the art in view of the foregoing description. Accordingly, this description is to be construed as illustrative only and is for the purpose of teaching those skilled in the art the best mode for carrying out the invention. The details of the structure and architecture may be varied substantially without departing from the spirit of the invention, and the exclusive use of all modifications which come within the scope of the appended claims is reserved.

What is claimed is:

1. A method of focused phosphene generation in retinal tissue through deeper intermediate retinal cellular electrical stimulation to the exclusion of direct ganglion cellular electrical stimulation comprising the steps of:

positioning at least one stimulating electrode in the vicinity of retinal tissue; and applying a long duration stimulation signal to the at least one electrode such that deeper intermediate retinal cells are preferentially stimulated over the retinal ganglion cells and proximal overlying surface axons.

2. The method of claim 1, wherein the long duration stimulation signal is a biphasic signal having a negative and a positive phase pulse.

3. The method of claim 2, wherein said step of applying a long duration stimulation signal comprises the step of applying the long duration stimulation signal in cathodic fashion.

4. The method of claim 2, wherein the duration of the long duration stimulation signal is greater than about 0.5 millisecond per phase pulse.

5. The method of claim 2, wherein the duration of the long duration stimulation signal is greater than or equal to about 2 millisecond per phase pulse.

6. The method of claim 2, wherein the duration of the long duration stimulation signal is greater than about 4 millisecond per phase pulse.

7. The method of claim 2, wherein the duration of the long duration stimulation signal is greater than about 8 millisecond per phase pulse.

8. The method of claim 2, wherein said step of applying a long duration stimulation signal comprises the step of applying a train of said biphasic signals.

9. The method of claim 2, wherein said biphasic signal includes an intra-pulse delay.

10. The method of claim 9, wherein said intra-pulse delay is in relation to a duration of said negative pulse.

11. The method of claim 9, wherein said intra-pulse delay is in the range of about 1 to 4 millisecond.

12. The method of claim 2, wherein said step of applying a long duration stimulation signal comprises the step of adjusting said biphasic signal to simulate a monophasic signal.

13. The method of claim 12, wherein said step of adjusting said biphasic signal comprises the steps of:

adjusting a magnitude of said negative pulse in relation to said positive pulse; and adjusting a duration of said positive pulse in relation to said negative pulse to maintain approximately net zero charge introduction.

14. The method of claim 13, wherein said step of adjusting a magnitude of said negative pulse in relation to said positive pulse increases the magnitude of the negative pulse by a ratio of approximately 10:1 to the positive pulse.

15. The method of claim 1, wherein the long duration stimulation signal is a periodic waveform having a frequency less than or equal to about 50 hertz.

16. The method of claim 1, wherein the long duration stimulation signal has a duration and a magnitude selected to preclude inadvertent stimulation of retinal ganglion cells.

17. A method of preferentially stimulating intermediate retinal elements comprising the steps of:

positioning a stimulating electrode in proximity to retinal tissue; and applying a biphasic stimulation signal having a duration greater than about 0.5 milliseconds to the electrode.

18. The method of claim 17, wherein said duration is greater than or equal to about 2 milliseconds.

19. The method of claim 18, wherein said step of applying a biphasic stimulation signal comprises the step of applying a biphasic stimulation signal in a cathodic fashion.

20. A method of producing focused phosphenes in retinal tissue comprising the steps of:

positioning a stimulating electrode in proximity to retinal tissue; and generating a biphasic stimulation signal having a negative and a positive pulse and including an intra-pulse delay therebetween, each of said pulses having a duration greater than or equal to about 2 milliseconds and a magnitude, said biphasic stimulation signal having a relationship between said magnitude and said duration of said negative and said positive pulses such that the total charge supplied is approximately zero; and applying said biphasic stimulation signal to the electrode in a cathodic fashion.

* * * * *